(12) United States Patent
Toop

(10) Patent No.: US 8,419,791 B2
(45) Date of Patent: Apr. 16, 2013

(54) INTRAOCULAR LENS WITH ONE OR MORE COMPRESSIBLE HAPTICS

(75) Inventor: Peter Toop, Bucks (GB)

(73) Assignee: Rayner Intraocular Lenses Limited, Buckinghamshire (GB)

( * ) Notice: Subject to any disclaimer, the term of this patent is extended or adjusted under 35 U.S.C. 154(b) by 1136 days.

(21) Appl. No.: 11/505,726

(22) Filed: Aug. 17, 2006

(65) Prior Publication Data
US 2006/0276892 A1 Dec. 7, 2006

Related U.S. Application Data

(63) Continuation of application No. 10/629,272, filed on Jul. 29, 2003, now abandoned.

(30) Foreign Application Priority Data

Jul. 30, 2002 (GB) .................................. 0217606.3

(51) Int. Cl.
*A61F 2/16* (2006.01)
(52) U.S. Cl.
USPC ...................... 623/6.16; 623/6.44; 623/6.51
(58) Field of Classification Search ................. 623/6.11, 623/6.15–6.21, 6.38–6.43, 6.46, 6.49, 6.51–6.53, 623/6.55
See application file for complete search history.

(56) References Cited

U.S. PATENT DOCUMENTS

| | | | |
|---|---|---|---|
| 4,562,600 A | 1/1986 | Ginsberg et al. | |
| 5,074,875 A | 12/1991 | Donn et al. | |
| 5,376,116 A * | 12/1994 | Poler | 623/6.16 |
| 6,162,249 A | 12/2000 | Deacon et al. | |
| 6,190,410 B1 * | 2/2001 | Lamielle et al. | 623/6.51 |
| 6,200,344 B1 | 3/2001 | Lamielle et al. | |
| 6,468,306 B1 * | 10/2002 | Paul et al. | 623/6.16 |
| 6,596,025 B2 * | 7/2003 | Portney | 623/6.17 |
| 2002/0095211 A1 | 7/2002 | Young | |

FOREIGN PATENT DOCUMENTS

| | | |
|---|---|---|
| EP | 0962196 | 12/1999 |
| EP | 1 138 282 A1 * | 10/2001 |
| WO | WO 98/05273 A1 * | 2/1998 |

OTHER PUBLICATIONS

Hansen, S. O. et al., "Posterior capsular opacification and intraocular lens decentration. Part I: Comparison of various posterior chamber lens designs implanted in the rabbit model," *J Cataract Refract Surg.*, Nov. 1988, pp. 605-613, vol. 14.

Vargas, L. G. et al., "Implantation of a new low power foldable posterior chamber intraocular lens in a rabbit model. Cliniopathological study with special reference to posterior capsule opacification," Presented in part at the XX Congress of the European Society of Cataract and Refractive Surgeons (ESCRS), Sep. 2002, Nice, France, 26 pages.

* cited by examiner

*Primary Examiner* — David H. Willse
(74) *Attorney, Agent, or Firm* — Saliwanchik, Lloyd & Eisenschenk

(57) ABSTRACT

An intraocular lens comprises an optic and one or more haptics, wherein the or each haptic can be compressed in the plane of the lens, and which additionally comprises, around the optic, an annular rim that, in use, is in contact with the posterior capsular sac.

12 Claims, 4 Drawing Sheets

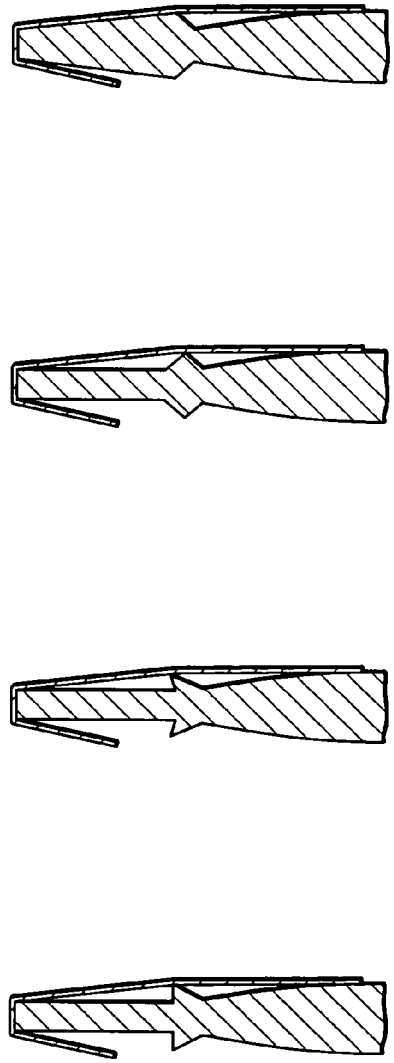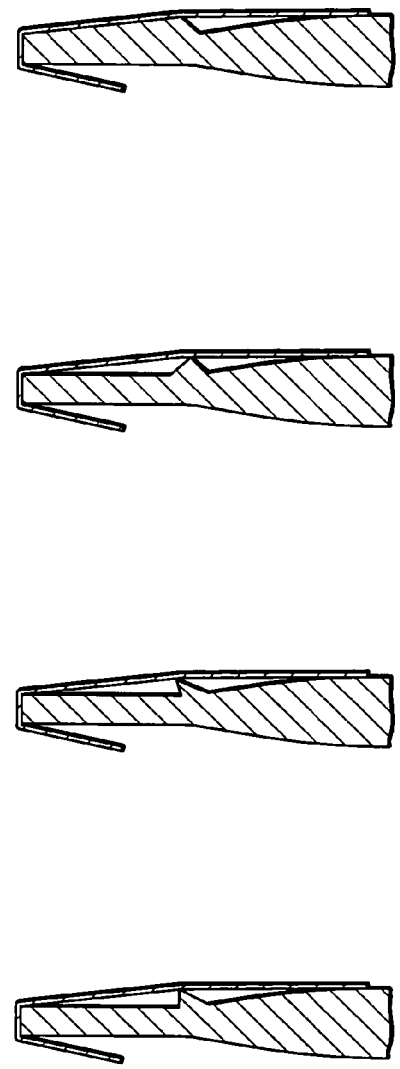

INTRAOCULAR LENS WITH ONE OR MORE COMPRESSIBLE HAPTICS

This application is a continuation application of Ser. No. 10/629,272, filed Jul. 29, 2003, now abandoned; which claims priority to Great Britain Application No. 0217606.3, filed Jul. 30, 2002.

FIELD OF THE INVENTION

This invention relates to an intraocular lens which, in use, inhibits posterior capsular opacification.

BACKGROUND OF THE INVENTION

Posterior capsular opacification (PCO) is a common long-term complication of cataract surgery. During cataract surgery, the central anterior lens capsule is removed and the natural lens replaced with an artificial intraocular lens. The posterior lens capsule remains intact. After surgery, viable epithelial cells of the natural lens may remain in the lens capsule equator. These cells can migrate across the inner surface of the posterior capsule, causing it to opacify. The effect, i.e. PCO, is similar to a cataract and for this reason is sometimes called "secondary cataract". PCO is age-related, occurring more in children rather than adults.

The standard treatment for PCO is neodymium: yttrium-aluminium-garnet (Nd-YAG) laser posterior capsulotomy. The laser is used to create an opening in the centre of the posterior capsule, to produce a clear area for light to reach the retina. Although the procedure is non-invasive, complications such as retinal detachment and lens damage may arise.

EP-A-0962196 describes an intraocular lens wherein the haptics are shaped such that, in a first stage of compression, the proximal part of the haptic can be fully compressed; and in a second stage, the distal part of the haptic can be compressed, to provide a lens that is eventually resistant to haptic failure.

A number of lenses for the prevention of PCO have been proposed, but on the whole, little if any reduction in PCO has been achieved. There still exists the need for an intraocular lens which is effective at reducing PCO.

SUMMARY OF THE INVENTION

An intraocular lens of the present invention comprises an optic and one or more haptics, wherein the or each haptic can be compressed in the plane of the lens, and which additionally comprises, around the optic, an annular rim that, in use, is in contact with the posterior capsular sac. The annular rim is preferably present on both the posterior and anterior surfaces of the lens; this facilitates insertion of the lens since the surgeon may not need to distinguish between the two surfaces.

The thickness (i.e. the depth) of the annular rim is preferably greatest in a region proximal to the or each haptic. This allows easier folding of the lens and insertion through a smaller incision. The change in the thickness of the rim is preferably gradual.

Preferably, the or each haptic is curved and shaped such that, in a first stage of compression, the proximal part of the haptic can be fully compressed, and, in a second stage, the distal part of the haptic can be compressed. This two-stage compression has been shown to be particularly effective in maintaining contact between the rim and the sac.

Lenses of the invention are effective at inhibiting PCO. Haptic compression allows contact between the rim of the optic and the posterior chamber to be maintained, thus preventing the migration of epithelial cells into the posterior lens region.

BRIEF DESCRIPTION OF THE DRAWINGS

FIGS. 4A to 4D are cut-away side views of four lenses of the invention. Each lens comprises an annular rim on the posterior and anterior faces; each lens has a rim of different geometry with respect to the others.

FIGS. 5A to 5D are similar to FIGS. 4A to 4D, except that the lenses only comprise an annular rim on the posterior face.

DESCRIPTION OF THE PREFERRED EMBODIMENTS

The size of the annular rim is preferably minimised to allow the optic to be as large as possible. Intraocular lenses are generally inserted into the eye using an injector; in this case, a lens of the invention must be able to withstand the forces of injection.

A lens of the invention may comprise an optic of negative and/or positive powers. Typical negative powers, but not limited thereto, are −10 to −1 Diopters. Typical positive powers but not limited thereto are +1 to +34 Diopters.

Since the shape/size of the annular rim is proportional to the power of the optic, it may be possible to express this relationship mathematically. This may allow the size of the rim to be calculated simply by determining a patient's optical power.

Embodiments of the invention will now be described by way of example with reference to the accompanying drawings.

Figure 1:
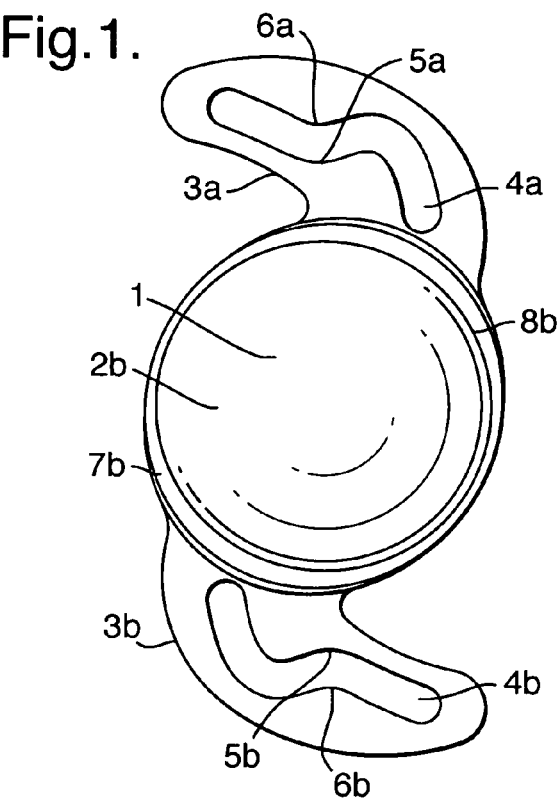
FIG. 1 is a plan view of an intraocular lens embodying the present invention.

FIG. 1 shows an intraocular lens having an optic 1, comprising convex faces (the posterior face 2b, is shown) and haptics 3a and 3b. Each haptic comprises an aperture, respectively 4a and 4b. Opposed points of each aperture, at 5a and 6a, and 5b and 6b, are shown.

These features are such that initial compression of the haptic leads to abutment of opposite walls of the aperture, bringing the opposed points 5a and 6a, and 5b and 6b, into contact, thereby defining a proximal part that is fully compressed and a distal part that can undergo further compression. Such further compression brings the distal end of each haptic substantially into contact with the periphery of the optic, to give an essentially elliptical shape, in plan.

The lens comprises an annular rim on each of the anterior and posterior faces of the optic, respectively; the posterior rim 7b is shown. The periphery of the posterior optic face 8b is also shown. As seen in the Figures (e.g., FIGS. 2A-2C, 3B, 4A-4D, and 5A-5D), each annular rim can be homogeneously formed with the optic.

The haptics hold the capsular sac tight against the posterior annular rim, such that epithelial cells are prevented from migrating to the optic region. This inhibits the onset of PCO.

Figure 2C:
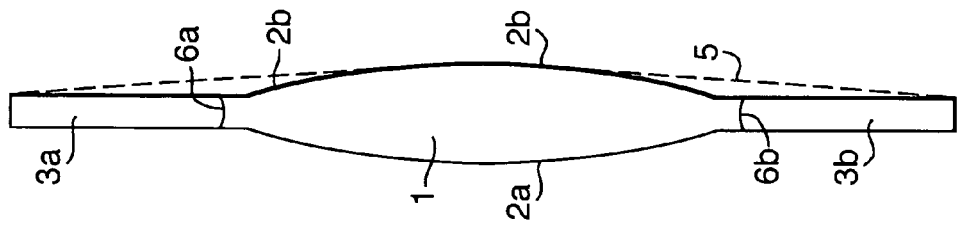
FIGS. 2A to 2C are side views of intraocular lenses which, with the exception of FIG. 2C, embody the present invention.
Figure 2B:
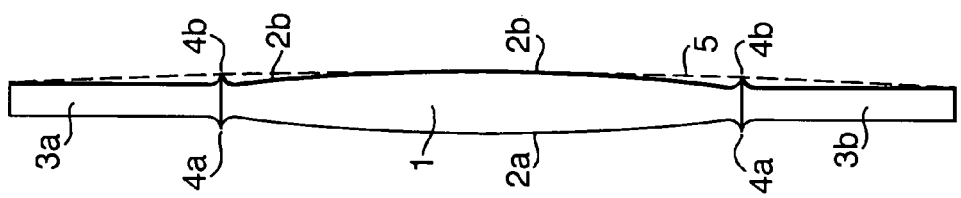
Figure 2A:
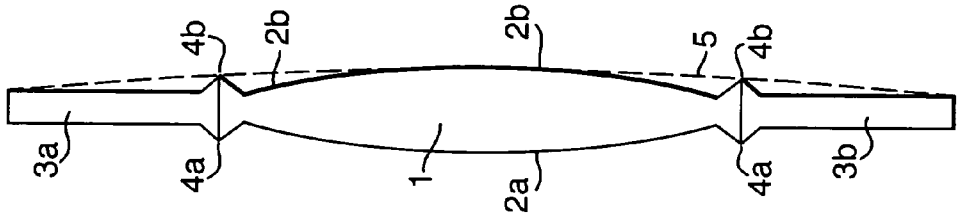

FIGS. 2A and 2B show lenses of the invention, each comprising a biconvex optic 1, having an anterior face 2a and a posterior face 2b. The lenses comprise compressible haptics 3a and 3b, and annular rims 4a and 4b. In each case, the posterior capsular sac 5 compresses the haptics, such that the posterior annular rim 4b is held tight against the posterior sac. The lens of FIG. 2A is of higher power than that of FIG. 2B, and requires a thicker annular rim since the biconvex optic is wider.

FIG. 2C shows a conventional planar haptic PCO retarding lens. Instead of comprising an annular rim, the edge surfaces of the optic in contact with the haptic (6a and 6b) are effectively tapered. These tapered edges fail to prevent cell migration since there still exists gaps between the posterior capsular sac and the lens edge. Cells may migrate through this gap, resulting in PCO.

Figure 3A:
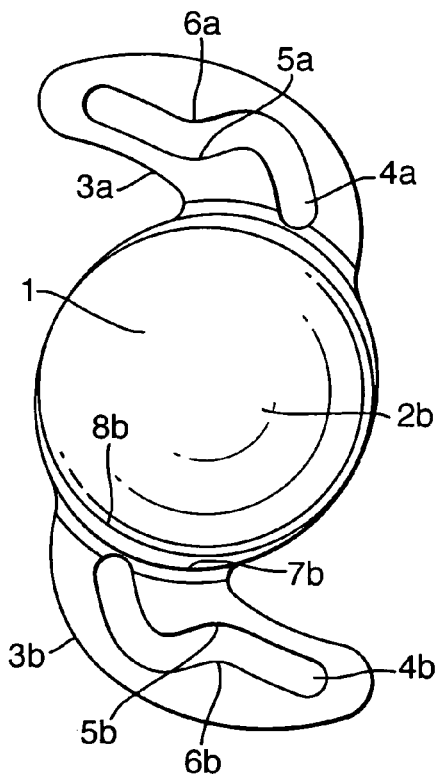
FIGS. 3A and 3B are respectively plan and cut-away side views of a lens of the invention in which the thickness of the annular rim is greatest in the region of the optic binding the haptic.
Figure 3B:
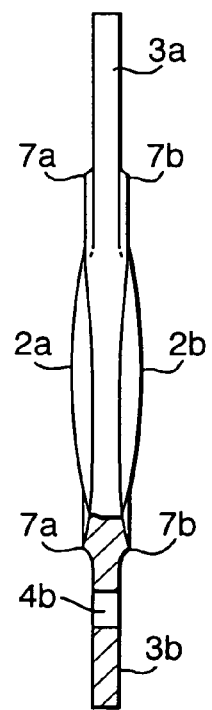

FIGS. 3A and 3B show a lens similar to that of FIG. 1 except in that the thickness of the annular rims is greatest in the region of the optic binding the haptic.

FIGS. 4A to 4D illustrate a range of rim geometries which may be suitable for use in the present invention. The lenses are shown in relation to the posterior capsular sac. Each lens has a different rim geometry. Particular reference is made to the lens of FIG. 4D, where the rim and haptic effectively act as a single unit, pressing fast against the posterior capsular sac.

FIGS. 5A to 5D show similar rim geometries to those in FIGS. 4A to 4D, except that each lens only comprises a rim on the posterior face.

Figure 6A:
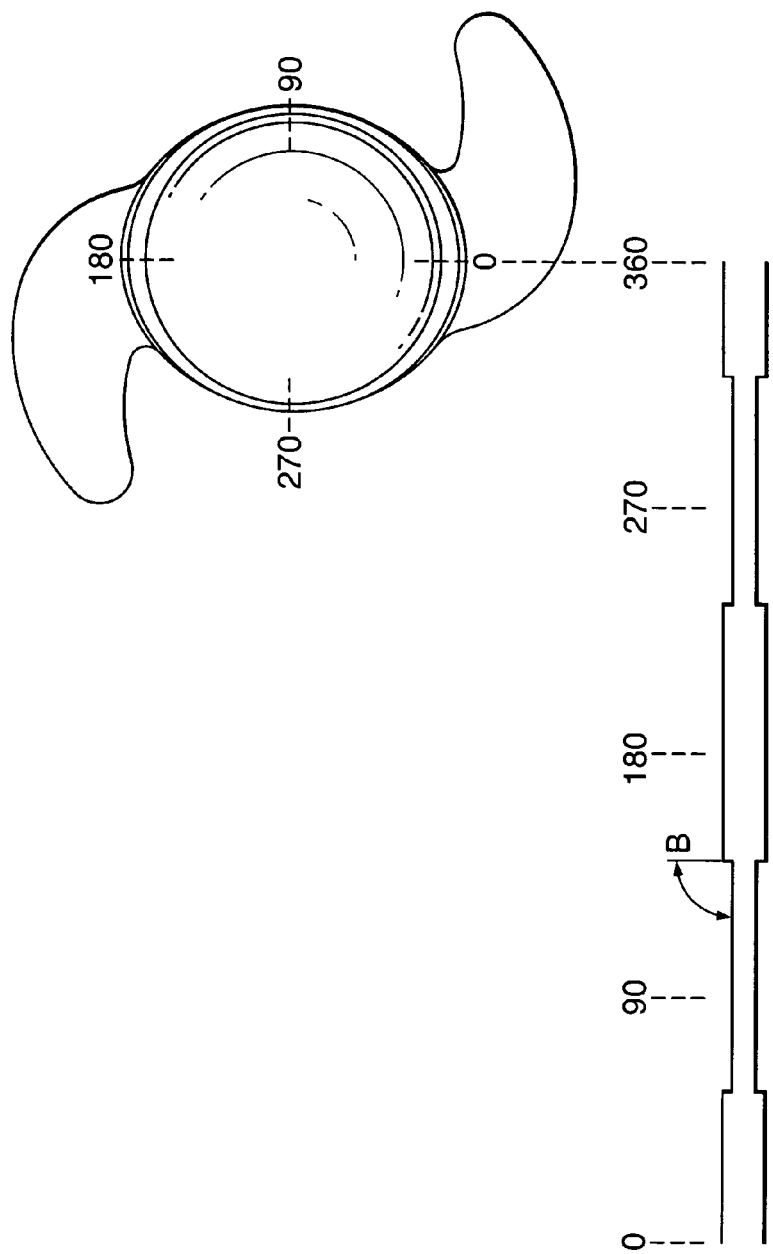
FIGS. 6A and 6B are "roll-out" representations of two lenses of the invention, i.e. they are views of the complete optic edge. A plan view of a lens of the invention is also shown, to clarify where a point on a "roll-out" representation corresponds to a position on the optic circumference.
Figure 6B:

FIGS. 6A and 6B are "roll-out" representations of optic edges of two lenses of the invention. In general, it is desirable to reduce the optic width at the points 90° and 270° (as shown in FIGS. 6A and 6B) because a known adverse effect of thick optic edges is an increased risk of glare from internal reflections.

FIG. 6A shows a lens of the invention where the edge of the optic abruptly changes from thick to thin. Such an abrupt change is not ideal since slight pressure from the vitreous may be insufficient to force the posterior capsule into the "corner" regions such as that indicated by the angle B.

FIG. 6B shows a preferred embodiment of the invention, in which there is a gradual change of edge thickness, allowing a full (i.e. 360°) seal between the barrier and the capsule, substantially reducing any edge glare effects. Angle A is preferably less than 15°.

The following Example illustrates the invention.

EXAMPLE

Experiments were performed to compare the extent of PCO resulting from the use of a known intraocular lens "A" (570H Centerflex™ lens, Rayner intraocular Lenses Ltd.,), and a lens of the invention "B" (570C). Essentially, lens B is the same as lens A except that it comprises an annular rim.

All lenses used in this study had an optic body diameter of 5.75 mm and a refractive power of +21 D. Five IOLs of each type were used. The lenses were implanted in a randomised manner by the same surgeon.

Dutch Belted pigmented rabbits weighting 2.4-3.0 kg were used. Each animal was prepared for surgery by pupil dilation with 1% cyclopentolate hydrochloride and 2.5% phenylephrine drops, applied topically every 5 minutes for 15 minutes. Anesthesia was obtained with an intramuscular injection of ketamine hydrochloride (50 mg/kg) and xylazine (7 mg/Kg) in a mixture of 7:1, respectively. One drop of topical proparacaine hydrochloride anesthetic was also placed in each eye prior to beginning surgery. The area around the eye was draped in an aseptic manner, and a lid speculum was placed to retract the lids.

Using aseptic technique and a Zeiss surgical microscope, a fornixed-based conjunctival flap was fashioned. A 3.2-mm partial thickness limbal incision was then made using a beaver blade and the anterior chamber was entered. One ml of heparin (10,000 units/ml) was injected into the anterior chamber, followed by injection of a viscoelastic material (Amvisc Plus™, Bausch & Lomb). A capsulorhexis forceps was used to create a continuous curvilinear capsulotomy, with a diameter of around 4.5 to 5.0 mm. The phaco handpiece (Alcon Coopervision Series 10,000) was inserted into the posterior chamber for removal of lens nucleus and cortical material. 0.5 ml of epinephrine 1:1000 and 0.5 ml of heparin (10,000 USP units/ml) were added to each 500 ml of irrigation solution to facilitate pupil dilation and control inflammation. The endocapsular technique was used with the phacoemulsification to take place entirely within the capsular bag. Any residual cortex was then removed with the same handpiece. After removal of the lens, a viscoelastic was used to inflate the capsular bag. The IOLs were then inserted into the capsular bag using the manufacturer's recommended injector system (Rayner titanium injector). Wound closure was achieved with 10.0 monofilament nylon suture after aspiration of viscoelastic material.

Combination antibiotics/steroid ointment (neomycin and polimixin B sulfates, and dexamethasone) was applied to the eyes following surgery. The same ointment was placed in the rabbit eyes four times per day for the first postoperative week. This was then discontinued after one week. In the second postoperative week each animal received topical prednisolone acetate drops four times per day with discontinuation of the drops following the second postoperative week.

All eyes were evaluated by slit lamp examination and scored for ocular inflammatory response at one week, two weeks and three weeks post-operatively. A standard scoring method in different specific categories was used at each examination, including assessment of corneal edema, as well as the presence of cell and flare within the anterior chamber. PCO was evaluated under retro-illumination with the pupil fully dilated.

After the final clinical examination at three weeks, the animals were anesthetised using a 1.6 ml intramuscular injection of a 7:1 mixture of ketamine hydrochloride and xylazine, and then humanely euthanised with a 1 ml intravenous injection of pentobarbital sodium/phenytoin sodium (Euthasol®, Delmarva Laboratories). Their globes were enucleated and placed in 10% neutral buffered formalin for twenty-four hours. The globes were then bisected coronally just anterior to the equator. Gross examination and photographs from the posterior aspect (Miyake-Apple view) were performed to assess the PCO development. The intensity of central and peripheral PCO was scored from grades 0-4; see Hansen et al, J. Cataract Refract. Surg. 14:605613 (1988), for details of the method of scoring.

Table 1 summarises the results of the PCO scoring done from a posterior (Miyake-Apple) view. In Table 1, OD (oculus dexter) refers to the right eye, OS (oculus sinister) to the left. In each eye, central and peripheral PCO scores were lower for lens B, and higher for lens A. The average central PCO scores for lenses A and B were 0.90 and 0.39 respectively. The average peripheral scores for A and B were 1.85 and 0.83 respectively. This illustrates the desirability of a lens of the invention.

TABLE 1

| Central PCO | | Peripheral PCO | |
| --- | --- | --- | --- |
| A | B | A | B |
| 0 | 0.5 | 3 | 1 |
| 1 | 1 | 2 | 1 |
| 1 | 0.5 | 2 | 1 |
| 1 | 0 | 2 | 0 |
| 2.5 | 0 | 3 | 1 |
| 0 | 0 | 2 | 1 |
| 1 | 1 | 2 | 2 |
| 1 | 0.5 | 1 | 0.5 |
| 1 | 0 | 1 | 0 |
| 0.5 | 0 | 0.5 | 0 |

The invention claimed is:

1. An intraocular lens having a plane normal to an eye's optical axis, said lens comprising an optic having an anterior face and one or more haptics,
wherein the, or each, haptic can be compressed in the plane of the lens,
wherein the, or each, haptic has a proximal part and a distal part,
wherein the, or each, haptic is curved, and shaped such that, in a first stage of compression, the proximal part of the haptic can be fully compressed, and, in a second stage, the distal part of the haptic can be compressed,
wherein the lens additionally comprises, on a posterior face of the optic, an annular rim having a pointed cross-section, wherein the rim is configured to contact the posterior capsular sac,
wherein the lens additionally comprises an annular rim on the anterior face of the optic, and
wherein the lens is configured such that it does not cause posterior vaulting and it does not cause anterior vaulting.

2. The lens according to claim 1, wherein the lens is adapted so that the optic is configured to touch the posterior capsular sac.

3. The lens according to claim 1, wherein the, or each, haptic includes an aperture of which opposed points are brought into contact, in the first stage of compression.

4. The lens according to claim 1, wherein the first, second, or each, stage of compression is essentially continuous, full compression being reached gradually from the proximal end towards the distal end of the haptic.

5. The lens according to claim 1, wherein each annular rim is thicker in a region proximal to the, or each, haptic.

6. The lens according to claim 5, wherein each annular rim comprises a gradual change in thickness.

7. The lens according to claim 1, wherein each annular rim is homogeneously formed with the optic.

8. An intraocular lens having a plane normal to an eye's optical axis, said lens comprising an optic having an anterior face and one or more haptics,
wherein the, or each, haptic can be compressed in the plane of the lens which contains the, or each, haptic,
wherein the, or each, haptic has a proximal part and a distal part,
wherein the lens additionally comprises, on a posterior face of the optic, a first annular rim having a pointed cross-section, wherein the rim is configured to contact the posterior capsular sac,
wherein the lens also comprises an annular rim on the anterior face of the optic, and
wherein the lens is configured such that it does not cause posterior vaulting and it does not cause anterior vaulting.

9. The lens according to claim 8, wherein the lens is adapted so that the optic is configured to touch the posterior capsular sac.

10. The lens according to claim 8, wherein each annular rim is thicker in a region proximal to the, or each, haptic.

11. The lens according to claim 10, wherein each annular rim comprises a gradual change in thickness.

12. The lens according to claim 8, wherein each annular rim is homogeneously formed with the optic.

* * * * *

UNITED STATES PATENT AND TRADEMARK OFFICE
CERTIFICATE OF CORRECTION

| | | Page 1 of 1 |
|---|---|---|
| PATENT NO. | : 8,419,791 B2 | |
| APPLICATION NO. | : 11/505726 | |
| DATED | : April 16, 2013 | |
| INVENTOR(S) | : Toop | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1258 days.

Signed and Sealed this
Sixteenth Day of December, 2014

Michelle K. Lee
*Deputy Director of the United States Patent and Trademark Office*